US00PP32554P2

(12) United States Plant Patent
Murray

(10) Patent No.: US PP32,554 P2
(45) Date of Patent: Dec. 1, 2020

(54) ***LOMANDRA* PLANT NAMED 'POM POM'**

(50) Latin Name: ***Lomandra confertifolia* ssp *pallida***
Varietal Denomination: POM POM

(71) Applicant: Joseph Murray, Cape Woolamai (AU)

(72) Inventor: Joseph Murray, Cape Woolamai (AU)

( * ) Notice: Subject to any disclaimer, the term of this patent is extended or adjusted under 35 U.S.C. 154(b) by 0 days.

(21) Appl. No.: 16/873,383

(22) Filed: Apr. 3, 2020

(51) Int. Cl.
*A01H 5/02* (2018.01)
*A01H 6/12* (2018.01)

(52) U.S. Cl.
USPC ..... Plt./263.1

(58) Field of Classification Search
USPC ..... Plt./373, 263.1
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct cultivar of *Lomandra* plant named 'POM POM' is disclosed, characterized by a small plant size, lime green foliage, semi-erect to arching foliage and increased flowering. The new variety is a *Lomandra*, typically produced as an outdoor ornamental plant.

2 Drawing Sheets

Latin name of the genus and species: *Lomandra confertifolia* ssp *pallida*.

Variety denomination: 'POM POM'.

BACKGROUND OF THE INVENTION

The new cultivar is the product of chance discovery. The new variety originated as a naturally occurring whole plant mutation found in a private planting of *Lomandra confertifolia* ssp *pallida* 'Lomion', U.S. Plant Pat. No. 23,034, also known as 'Lime Tuff'.

The new variety was first selected by the inventor, during October of 2014, in Victoria, Australia. Date of first sale was May 7, 2019, occurring in Australia. This sale was made directly by the inventor or one who obtained the claimed invention directly or indirectly from the inventor. This sale and all public disclosures made between May 2019 and the filing of this application fall within the exception allowed under 102(b)(1).

First asexual reproduction of the new cultivar 'POM POM' was first performed by tissue culture during 2016 in Pakenham, Australia. Access to all plants was restricted, as plants were kept in a location not open to the public. Through subsequent propagation, multiple generations have been reproduced, which have shown that the unique features of this cultivar are stable and reproduced true to type.

SUMMARY OF THE INVENTION

The cultivar 'POM POM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'POM POM' These characteristics in combination distinguish 'POM POM' as a new and distinct *Lomandra* cultivar:

1. Short plant habit.
2. Semi-erect to arching habit.

3. Strong flowering.
4. Lime green foliage.

PARENT COMPARISON

Plants of the new cultivar 'POM POM' are similar to the parent in most horticultural characteristics. The new variety, however, differs in the following ways:

1. The new variety has a narrower leaf.

COMMERCIAL COMPARISON

Plants of the new cultivar 'POM POM' are similar to the commercial variety *Lomandra* 'Little Lime', unpatented in most horticultural characteristics. The new variety, however, differs in the following:

1. 'POM POM' produces more flowers than 'Little Lime'.
2. 'POM POM' has semi-erect to arching foliage, 'Little Lime' has erect foliage.

BRIEF DESCRIPTION OF THE PHOTOGRAPHS

Figure 1:
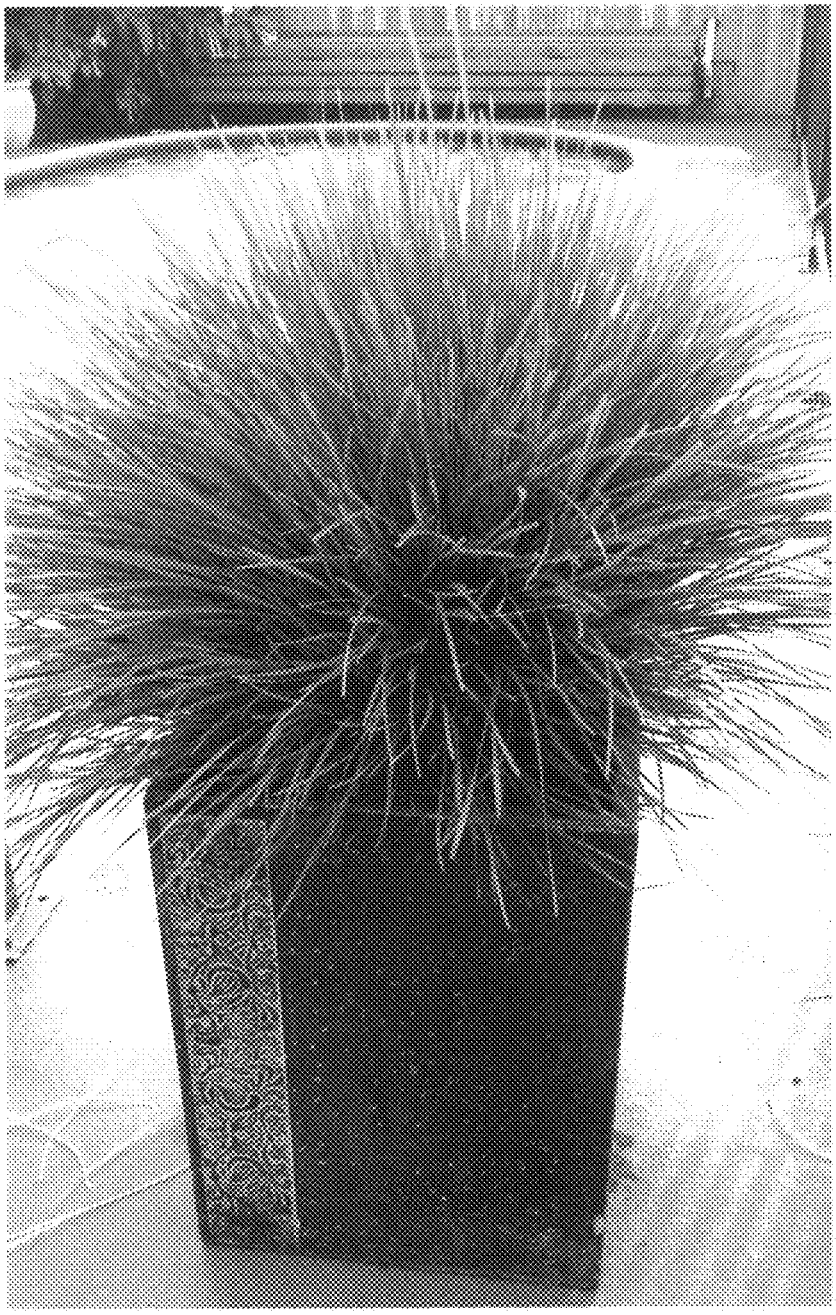

The accompanying photograph in FIG. 1 illustrates in full color a plant of 'POM POM' at about 2 years of age. The semi-erect to arching foliage is illustrated.

Figure 2:
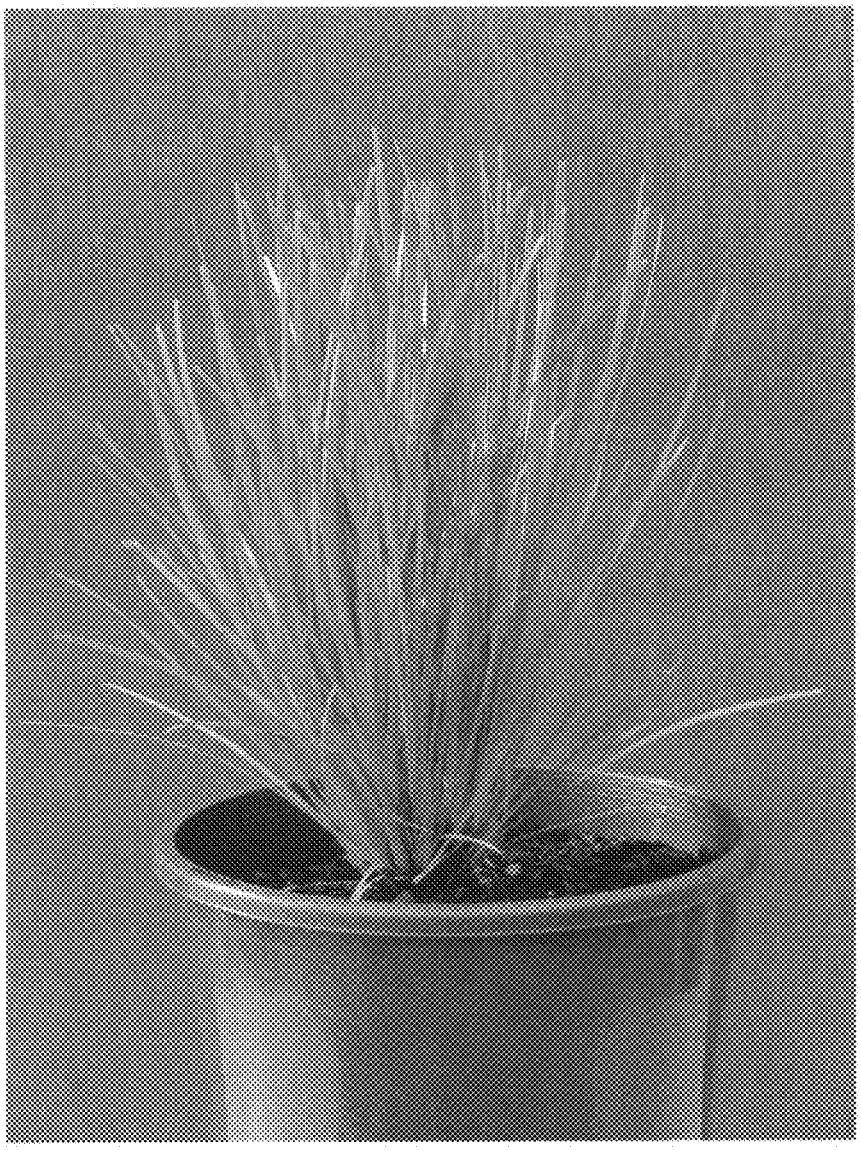

FIG. 2 illustrates in full color a close up a young plant from tissue culture 'POM POM' at about 3-4 months from planting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'POM POM' plants grown outdoors in Victoria, Australia. Plants are approximately 1 year old. Temperatures ranged from approximately 8° C. to 15° C. at night and 10° C. to 40° C. during the day. No artificial light, photoperiodic treatments were given to the plants. No chemical treatments were given to plants. Measurements and numerical values represent averages of typical plant types.

Botanical classification: *Lomandra confertifolia* ssp *pallida* 'POM POM'.

PROPAGATION

Root description: Fibrous roots, tan to brown, not accurately measured with R.H.S. chart.

PLANT

Growth habit: Clump/tuft forming perennial grass-type plant with semi-erect to arching foliage. Plants evergreen to −8° F.

Height: Foliar plane 90 cm. Flowering plane 90 cm.

Plant spread: Approximately 90-120 cm.

Growth rate: Moderate.

FOLIAGE

Leaf:

*Average leaf length*.—Average 59.55 cm

*Average leaf width*.—Average 4 mm.

*Arrangement*.—Tufts/clumps.

*Shape of blade*.—Linear.

*Apex*.—Praemorse.

*Base*.—Sheathed.

*Margin*.—Entire.

*Texture of top surface*.—Smooth.

*Texture of bottom surface*.—Smooth.

*Quantity of leaves per plant*.—Average 30 to 40.

*Color*.—Mature Upper surface: Near RHS Green 141B. Mature Lower surface: Near RHS Green 141B. Immature Upper surface: Near RHS Green 141B. Immature Lower surface: Near RHS Green 141B.

Venation: Linear, indistinguishable from leaf blade.

FLOWER

Natural flowering season: Spring and Summer.

Length of flowering period: Approximately 8 weeks.

Inflorescence type: Panicle, composed of male flowers only.

Individual flower type: Single, male.

Panicle size:

*Diameter*.—Average 2 to 3 cm.

*Height*.—Average 2 to 6 cm.

Bud:

*Shape*.—Ovate.

*Length*.—Approximately 2 to 3 mm.

*Diameter*.—Approximately 1 to 2 mm.

*Color*.—Near RHS Greyed-Orange 166A.

Corolla:

*Arrangement*.—Rotate, outward facing.

*Size*.—Depth: 2 to 3 mm. Diameter: 1 to 2 mm.

*Petals*.—

*Length*.—About 1-2 mm.

*Width*.—About 0.5 to 1 mm.

*Margin*.—Entire.

*Shape*.—Ovate.

*Apex*.—Acute.

*Texture*.—Glabrous all surfaces.

Color:

*Tepals*.—When opening: Outer surface: Near RHS Yellow 5A. Inner surface: Near RHS Yellow 5A. Fully opened: Outer surface: Near RHS Yellow 5A. Inner surface: Near RHS Yellow 5A. 93B. Color Changes when Aging: Outer surface: Near RHS Yellow 5A. Inner surface: Near RHS Yellow 5A.

Calyx: 1-2 mm long and about 1 mm in diameter. Colored red-brown, too small to accurately measure with color chart.

Fragrance: Moderate, sweet observed at night.

Peduncle:

*Length*.—Average range 40 to 50 cm.

*Diameter*.—5 mm, flattened.

*Texture*.—Glabrous.

*Color*.—Near RHS Green 143B.

Pedicel:

*Length*.—4 to 6 mm.

*Diameter*.—About 2 mm.

*Texture*.—Glabrous.

*Color*.—Near RHS Green 143B Fragrance: None.

OTHER CHARACTERISTICS

Stamen number: 6.

Stamen/anther size: Less than 0.5 mm.

Stamen/anther color: Near RHS Yellow 5A.

Pollen: Not observed.

Seed production: Sterile, no seed produced to date.

Disease resistance: Seems unaffected by any disease.

Temperature tolerance: Not tested but expected to handle −8° C. to 45° C.

Drought tolerance: Will tolerate considerable dryness once established.

What is claimed is:

1. A new and distinct cultivar of *Lomandra* plant named 'POM POM' as herein illustrated and described.

* * * * *